US012745919B2

(12) United States Patent
Lee et al.

(10) Patent No.: US 12,745,919 B2
(45) Date of Patent: Sep. 29, 2026

(54) METHOD OF MANUFACTURING SMART RING, AND SMART RING MANUFACTURED THROUGH THE METHOD

(71) Applicant: ZTACOM Co., Ltd., Seoul (KR)

(72) Inventors: Bum Yong Lee, Seoul (KR); Sang Il Lee, Seoul (KR); Ji Ha Hwang, Seoul (KR)

(73) Assignee: ZTACOM Co., Ltd., Seoul (KR)

( * ) Notice: Subject to any disclaimer, the term of this patent is extended or adjusted under 35 U.S.C. 154(b) by 715 days.

(21) Appl. No.: 18/022,723

(22) PCT Filed: Jan. 12, 2023

(86) PCT No.: PCT/KR2023/000561
§ 371 (c)(1),
(2) Date: Feb. 22, 2023

(87) PCT Pub. No.: WO2024/147394
PCT Pub. Date: Jul. 11, 2024

(65) Prior Publication Data

US 2025/0064332 A1 Feb. 27, 2025

(30) Foreign Application Priority Data

Jan. 3, 2023 (KR) ........................ 10-2023-0000591
Jan. 3, 2023 (KR) ........................ 10-2023-0000615

(51) Int. Cl.
*A61B 5/1455* (2006.01)
*A61B 5/026* (2006.01)
(Continued)

(52) U.S. Cl.
CPC ............ *A61B 5/026* (2013.01); *A61B 5/1455* (2013.01); *B05D 7/22* (2013.01);
(Continued)

(58) Field of Classification Search
CPC .................................................. A61B 5/1455
See application file for complete search history.

(56) References Cited

U.S. PATENT DOCUMENTS

2016/0166161 A1 6/2016 Yang et al.
2021/0265054 A1 8/2021 Kosman et al.

FOREIGN PATENT DOCUMENTS

CN 211022665 U 7/2020
KR 10-2321779 B1 11/2021
KR 10-2344609 B1 12/2021

*Primary Examiner* — Marjan Fardanesh
(74) *Attorney, Agent, or Firm* — Heedong Chae; Lucem, PC

(57) ABSTRACT

Disclosed are a method of manufacturing a smart ring and a smart ring manufactured through the method. The method of the present invention comprises: an outer cover unit processing process (S110) of processing and manufacturing an outer cover unit 100 having a ring shape of a smart ring and accommodating a sensor/communication module; a sensor/communication module manufacturing process (S120) of manufacturing the sensor/communication module 200 including a sensor module for sensing a biological signal of a smart ring user; an outer cover unit and sensor/communication module assembly manufacturing process (S200) of forming a ring-shaped outer cover unit and sensor/communication module assembly by accommodating the sensor/communication module 200 in the ring-shaped inside of the outer cover unit 100; an inner molded unit processing process (S300) of creating an inner molded unit 300 having a hole of a predetermined shape, into which a smart ring user's finger is inserted, inside the ring-shaped outer cover unit and sensor/communication module assembly; a sensing window forming process (S400) of forming a sensing window, which is an area that passes a signal or light needed for the sensor module to sense biological signals of the smart ring user, on an inner surface of the inner molded unit 300,
(Continued)

wherein in the inner molded unit processing process (S300), the inner molded unit 300 is created by filling a molding member in an entire inner area of the ring-shaped assembly, and cutting a hole of a predetermined shape at a center of the filled molding member.

11 Claims, 11 Drawing Sheets

(51) Int. Cl.
*B05D 7/22* (2006.01)
*B29C 45/14* (2006.01)
*G06F 1/16* (2006.01)
*B29L 31/00* (2006.01)

(52) U.S. Cl.
CPC ........ *B29C 45/14344* (2013.01); *G06F 1/163* (2013.01); *B29C 2793/0018* (2013.01); *B29L 2031/7096* (2013.01)

Conventional technique

METHOD OF MANUFACTURING SMART RING, AND SMART RING MANUFACTURED THROUGH THE METHOD

TECHNICAL FIELD

The present invention relates to a smart ring, and more specifically, to a method of manufacturing a smart ring that measures various activities or states of a body using a sensor module, and a smart ring manufactured through the method.

BACKGROUND ART

People in modern society have an interest in health higher than ever before as the average life expectancy increases. This interest breaks the stereotype that you should see a doctor only when you are sick, and leads to invention of a device that can continuously manage health even at normal times.

The device described above, which is commonly referred to as a wearable device, is a device emphasizing portability and freely worn on a body like as clothes, a watch, or glasses, and such wearable devices include smart glasses, smart watches, ring-shaped wearable devices, and the like.

"Wearable electronic device and manufacturing method thereof" is disclosed in US Patent Registration No. 9861314B2, which is a prior art related to the ring-shaped wearable devices among them.

This conventional technique discloses a method of manufacturing a smart ring comprising: a molded body of a moldable ceramic material, including an inner surface, an outer surface, and at least one cavity arranged on the inner surface and having a depth; an electronic part arranged in the cavity and having a thickness smaller than the depth of the cavity; and a coating of an epoxy material formed along the inner surface of a body part to cover the electronic part and the cavity using a molding device and a molding method of the conventional technique.

The smart ring, which is manufactured according to the manufacturing method of the prior art using the molding system of the conventional technique described above, is implemented to have an inner shape and a size of the smart ring predetermined according to the fixed shape and size of the inner surface of the already molded body.

Accordingly, when the smart ring manufacturing method of the conventional technique including the manufacturing method of the prior art is used, when it is required to change circuit components or move their locations, or to form a protrusion such as a sensor or the like on the inner surface of the smart ring or change its location, or when it is required to change the shape and size of the inner side of the smart ring according to a design intention, a plurality of molding parts and their settings, such as a mold or the like of a molding device, required for a new body having a different inner shape and size needs to be prepared according to different inner shapes and sizes in order to mold and manufacture the new body. Accordingly, the smart ring method of manufacturing the conventional technique including the manufacturing method of the prior art has a problem in that it is difficult to meet various demands related to the inner shape and size of the smart ring.

In addition, in order to implement a smart ring having an inner surface of various shapes and sizes in the smart ring manufacturing method of the conventional technique including the manufacturing method of the prior art, the number of equipment such as a mold, coating device, and the like increases in proportion to the various shapes and sizes, and additional time is required for individual settings thereof, and therefore, there is a problem in that the time and cost for developing and manufacturing smart rings of various shapes and sizes increase.

Furthermore, when a molding of an epoxy material is formed along the inner surface of the smart ring using the smart ring manufacturing method of the conventional technique including the manufacturing method of the prior art and a molding device used therefor, there is a limit in adjusting the transparency of the inner surface of the smart ring as the transparency is determined by the surface condition of the molded part on the inner surface of the molding device, and a separate polishing process is required to make a beautiful surface of a product. Accordingly, there is a problem in that product quality is lowered or the production process is complicated and inefficient.

Furthermore, when a molding of an epoxy material is formed along the inner surface of the smart ring using the molding device and molding method of the conventional technique as shown in FIG. 11, as the area of an epoxy injection unit, which functions as an outlet of air bubbles generated in the normally injected epoxy, is small, it takes a long time to remove the air bubbles or it is impossible to remove the air bubbles sufficiently, and there is a problem in that product quality is lowered.

PRIOR ART LITERATURE

US Patent Registration No. 9861314B2 (Jan. 9, 2018)

DISCLOSURE OF INVENTION

Technical Problem

Therefore, the present invention has been made in view of the above problems, and it is an object of the present invention to provide a new smart ring manufacturing method, which meets various demands related to the inner shape and size of a smart ring and reduces the time and cost for developing and manufacturing smart rings of various shapes and sizes, and a smart ring manufactured through the method.

In addition, according to embodiments, another object of the present invention is to provide a new smart ring manufacturing method, which is easy to adjust the overall transparency of the inner surface of the smart ring and the transparency of a part of the inner surface, and accordingly, may improve product quality related to the transparency and increase efficiency of the manufacturing process, and a smart ring manufactured through the method.

In addition, according to embodiments, another object of the present invention is to provide a new smart ring manufacturing method, which can improve accuracy of sensing biological signals of a sensor module and increase efficiency of related processes as it is possible to precisely process an area that passes a signal or light needed for the sensor module to sense biological signals of a smart ring user only with surface treatment of the inner surface since it is easy to adjust the overall transparency of the inner surface of the smart ring and the transparency of a part of the inner surface, and a smart ring manufactured through the method.

Furthermore, according to embodiments, another object of the present invention is to provide a new smart ring manufacturing method, which can reduce the time for removing air bubbles included in the molding and sufficiently remove the air bubbles when the inner surface of the smart ring is formed, and a smart ring manufactured through the method.

Technical Solution

To accomplish the above objects, according to one aspect of the present invention, there is provided a smart ring manufacturing method comprising: an outer cover unit processing process (S110) of processing and manufacturing an outer cover unit 100 having a ring shape of a smart ring and accommodating a sensor/communication module; a sensor/communication module manufacturing process (S120) of manufacturing the sensor/communication module 200 including a sensor module for sensing a biological signal of a smart ring user; an outer cover unit and sensor/communication module assembly manufacturing process (S200) of forming a ring-shaped outer cover unit and sensor/communication module assembly by accommodating the sensor/communication module 200 in the ring-shaped inside of the outer cover unit 100; an inner molded unit processing process (S300) of creating an inner molded unit 300 having a hole of a predetermined shape, into which a smart ring user's finger is inserted, inside ring-shaped the outer cover unit and sensor/communication module assembly; a sensing window forming process (S400) of forming a sensing window, which is an area that passes a signal or light needed for the sensor module to sense biological signals of the smart ring user, on the inner surface of the inner molded unit 300, wherein in the inner molded unit processing process (S300), the inner molded unit 300 is created by filling a molding member in the entire inner area of the ring-shaped assembly, and cutting a hole of a predetermined shape at the center of the filled molding member.

Preferably, the molding member of the inner molded unit 300 is a thermosetting plastic of a transparent material.

In addition, preferably, in the outer cover unit processing process (S110), the outer cover unit 100 is processed to include: an outer cover body 110 having a ring shape; an upper flange 120 provided on the top of the outer cover body 110; and a lower flange 130 provided on the bottom of the outer cover body 110, and a ring-shaped accommodation space surrounded by the inner surfaces of the outer cover body 110, the upper flange 120, and the lower flange 130 is formed.

Here, in the sensor/communication module manufacturing process (S120), the sensor/communication module 200 is preferably manufactured in a ring shape that can be accommodated in correspondence to the ring-shaped accommodation space by combining the components of the sensor/communication module 200.

Furthermore, preferably, the inner molded unit processing process (S300) includes: a molding member injection/curing process of injecting and curing the molding member in the entire inner area of the ring-shaped assembly of the outer cover unit and the sensor/communication module and removing the molding device; a horizontal cutting process of cutting a molding member protrusion unit protruding from at least one among the top and bottom surfaces of the ring-shaped assembly of the sensor/communication module filled with the cured molding member in the entire inner area; and a vertical cutting process of processing a hole of a predetermined shape at the center of the molding member filled in the ring-shaped assembly of the sensor/communication module filled with the molding member in the entire inner area without having a protrusion.

Here, the smart ring manufacturing method preferably further comprises a rounding unit processing process of forming a rounding unit 320 by rounding at least one among the top and bottom of the molded unit body 310 of the inner molded unit 300.

In addition, preferably, in the sensing window forming process (S400), a sensing window 330, which is a transparent or translucent area that passes a signal or light needed for an area corresponding to the position of the sensor module to sense biological signals, is formed by performing transparency-adjusted clear coating on the entire inner surface of the inner molded unit 300.

Furthermore, preferably, in the sensing window forming process (S400), a sensing window 330, which is an area that passes a signal or light needed for an area corresponding to a clear-coated sensor module to sense biological signals, is formed by performing transparency-adjusted clear coating in an area corresponding to the position of the sensor module of the inner molded unit 300.

Here, the sensing window forming process (S400) preferably includes: a masking process of attaching a masking member to an area of the smart ring to be processed, on which clear coating will not be performed; a primer coating process of forming a primer layer by applying a primer coating solution to the inner surface of the inner molded unit 300, on which clear coating will be performed; a process of forming a clear coating layer by applying a transparency-adjusted clear coating solution to a dried primer layer; and a drying and masking removal process of drying the clear coating layer and removing the masking member.

In addition, preferably, the molding device includes: an outer lower frame 410; an inner lower frame 420 coupled to the top of the outer lower frame 410, into which the lower portion of the assembly of the outer cover unit 100 and the sensor/communication module 200 is inserted and coupled; an inner upper frame 430 disposed on the top of the inner lower frame 420, into which the upper portion of the assembly of the outer cover unit 100 and the sensor/communication module 200 is inserted and coupled, and provided as an injection passage for the molding member; and an outer upper frame 440 disposed on the top of the inner upper frame 430 to fix the inner upper frame not to be spaced or separated, and the outer cover unit 100 includes a position guide 140 for guiding the outer cover body 110 at a set position of the molding device 400, wherein a first position guide protrusion 423 is provided on the outer wall of the inner lower frame 420 on the same vertical line as that of the position guide 140 and a second position guide protrusion 434, and the second position guide protrusion 434 is provided on the outer wall of the inner upper frame 430 on the same vertical line as that of the position guide 140 and the first position guide protrusion 423, in the molding member injection/curing process, coupling positions of the outer cover unit 100, the inner lower frame 420, and the inner upper frame 430 are guided using the position guide 140, the first position guide protrusion 423 and the second position guide protrusion 434.

According to another aspect of the present invention, there is provided a smart ring comprising: an outer cover unit 100 having a ring shape of a smart ring and accommodating a sensor/communication module; the sensor/communication module 200 including a sensor module accommodated in the outer cover unit 100 to sense a biological signal of a smart ring user; and an inner molded unit 300 having a hole of a predetermined shape, into which a smart ring user's finger is inserted, wherein the outer cover unit 100 and the sensor/communication module 200 are combined to form outer a ring-shaped cover unit and sensor/communication module assembly, and the inner molded unit 300 is formed by filling a molding member in the entire inner area of the ring-shaped assembly and cutting a hole of a predetermined shape at the center of the filled molding member.

Preferably, the outer cover unit 100 includes: an outer cover body 110 having a ring shape; an upper flange 120 provided on the top of the outer cover body 110; and a lower flange 130 provided on the bottom of the outer cover body 110, wherein a ring-shaped accommodation space surrounded by the inner surfaces of the outer cover body 110, the upper flange 120, and the lower flange 130 is formed, and the sensor/communication module 200 is accommodated and combined in the ring-shaped space.

Here, preferably, the sensor/communication module 200 is manufactured in a ring shape corresponding to the ring-shaped accommodation space surrounded by the inner surfaces of the upper flange 120 and the lower flange 130, and is accommodated and combined in the ring-shaped space surrounded by the inner surfaces of the outer cover body 110, the upper flange 120, and the lower flange 130.

In addition, here, the sensor/communication module 200 preferably includes: a base body 211 having a semicircular shape; a connection unit 212 having a semicircular shape and provided to be thinner than the base body 211, of which one side is coupled to the base body 211, and the other side is coupled to the plurality of PCB assemblies 215*a*, 215*b*, and 215*c*; the plurality of PCB assemblies 215*a*, 215*b*, and 215*c* of which one side is coupled to the connection unit 212; bending members 216 for connecting the PCB assemblies 215*a*, 215*b*, and 215*c*; and a connection member, of which one side is coupled to the base body 211, and the other side is coupled to the plurality of PCB assemblies 215*a*, 215*b*, and 215*c*.

In addition, preferably, the outer cover unit 100 includes a position guide 140 for guiding the outer cover body 110 at a set position of the molding device 400.

Furthermore, preferably, the molding member that forms the inner molded unit 300 is a cured transparent thermosetting plastic.

Here, a sensing window 330, which is an area that passes a signal or light needed for the sensor module to sense biological signals of a smart ring user, is preferably formed in the entire or part of the wall surface of the hole created by cutting the inner surface of the inner molded unit 300.

Here, the sensing window 330 is preferably an area whose transparency is improved by a clear coating layer at a position corresponding to the sensor module on the inner surface of the inner molded unit 300.

In addition, preferably, the sensor module includes an optical blood flow measurement sensor, and the sensing window 330 is at a position corresponding to the sensor module, and is a transparent or translucent area with improved transparency as a position corresponding to the position of the light emitting unit and the light receiving unit of the optical blood flow measurement sensor is clear-coated.

Advantageous Effects

According to the present invention as described above, it is possible to provide a new smart ring manufacturing method, which satisfies various demands related to the inner shape and size of a smart ring and reduces the time and cost for developing and manufacturing smart rings of various shapes and sizes, and a smart ring manufactured through the method.

According to the new smart ring manufacturing method of the present invention, as an inner molded unit 300 is formed by filling a molding member in the entire inner area of an assembly of a ring-shaped outer cover unit 100 and a sensor/communication module 200, and then processing a hole of a predetermined shape at the center of the filled molding member, there is an effect of implementing various inner shapes and sizes of a smart ring through an inner molded unit processing process including a simple cutting process even without a change in the molding device.

In addition, according to the new smart ring manufacturing method of the present invention and a smart ring manufactured through the method, there is an effect of easily adjusting the overall transparency of the inner surface of the smart ring and the transparency of a part of the inner surface, and accordingly, improving product quality related to the transparency and increasing efficiency of the manufacturing process.

According to embodiments, there is an effect of improving accuracy of sensing biological signals of a sensor module and increasing efficiency of related processes as it is possible to precisely process an area that passes a signal or light needed for the sensor module to sense biological signals of a smart ring user in a method of improving transparency of the entire or part of the inner surface of the smart ring through surface treatment, such as a clear coating, of the inner surface.

In addition, according to embodiments, through control of composition of a clear coating solution for improving transparency and masking, there is an effect of precisely adjusting transparency and controlling a part to which the transparency adjustment is applied.

Furthermore, in the new smart ring manufacturing method of the present invention, as a molding device that performs a molding member injection/curing process of the inner molded unit processing process (S300) may make the area of the molding member exposed to the outside wider as much as the wide area of the injection hole 431*a* in the inner frame structure, a large area is provided for air bubbles, generated by the use of the material of the molding member, to escape when the air bubbles are removed, and therefore, as the air bubbles may be easily discharged, the air bubbles can be removed quickly and more efficiently, compared to a molding device of the conventional technique having a small area exposed to the outside due to the small area of the injection hole. Accordingly, there is an effect of improving work efficiency and product quality related to transparency.

BEST MODE FOR CARRYING OUT THE INVENTION

Figure 1:
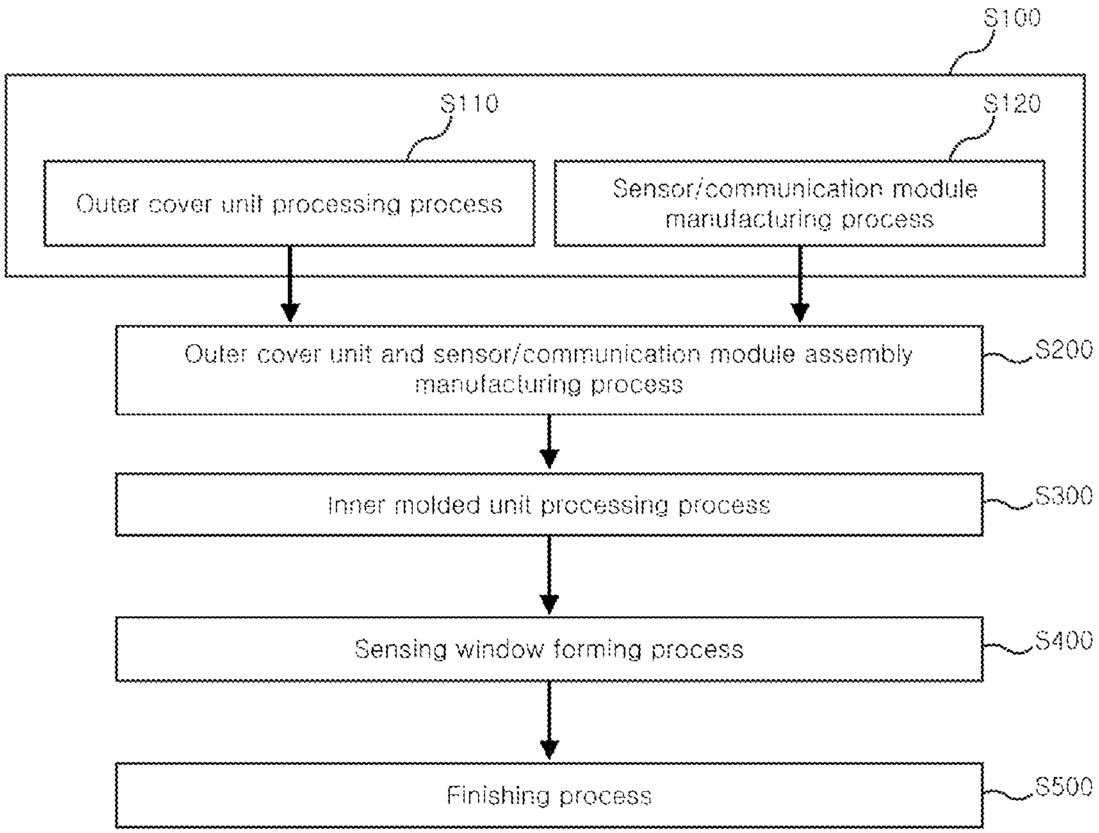
FIG. 1 is a flowchart illustrating a method of manufacturing a smart ring according to an embodiment of the present invention.

Hereinafter, details for embodying the present invention will be described based on embodiments with reference to the drawings. These embodiments are described in detail to be sufficient for those skilled in the art to embody the present invention. It should be understood that various embodiments of the present invention are not necessarily mutually exclusive although they are different from each other. For example, specific shapes, structures, and characteristics described herein may be implemented as s different embodiments without departing from the spirit and scope of the present invention. In addition, it should be understood that the locations or arrangements of individual components within each disclosed embodiment may be changed without departing from the spirit and scope of the present invention. Accordingly, the detailed description described below is not to be taken in a limiting sense, and the scope of the present invention, if properly described, is limited only by the appended claims, together with all the scopes equivalent to those claimed in the claims. Like reference numerals in the drawings indicate the same or similar function throughout various aspects.

Unless otherwise defined, all terms (including technical and scientific terms) used in this specification can be used as a meaning that can be commonly understood by those skilled in the art. In addition, terms defined in commonly used dictionaries are not interpreted ideally or excessively unless explicitly and specifically defined.

Hereinafter, preferred embodiments of the present invention will be described in detail with reference to the accompanying drawings so that those skilled in the art may easily embody the present invention.

Figure 2:
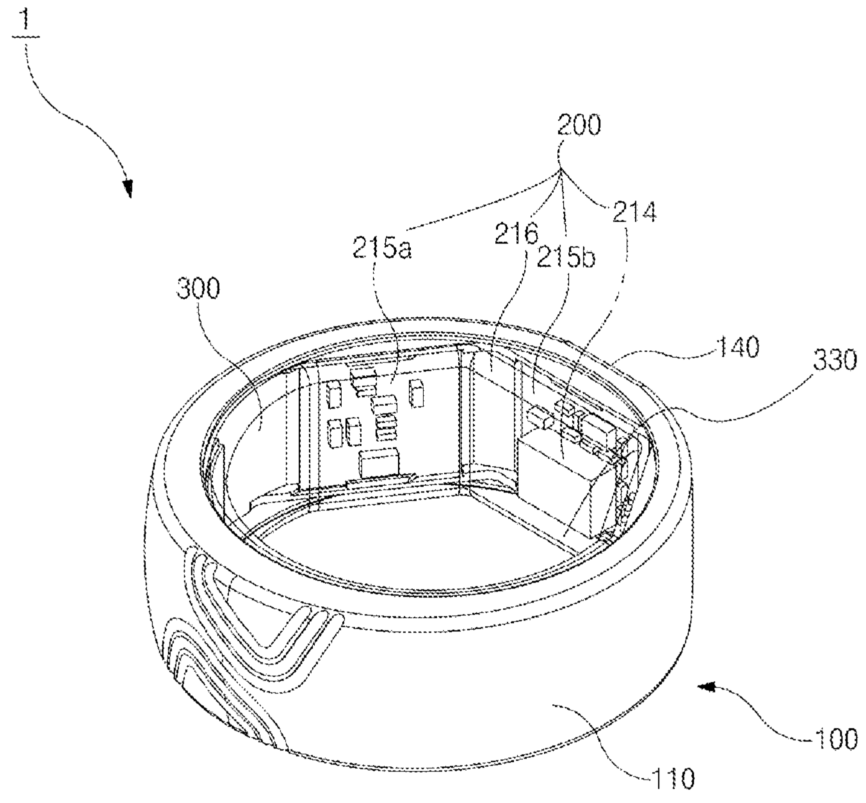
FIG. 2 is a perspective view showing a smart ring manufactured in the method of FIG. 1 according to an embodiment of the present invention.
Figure 3:
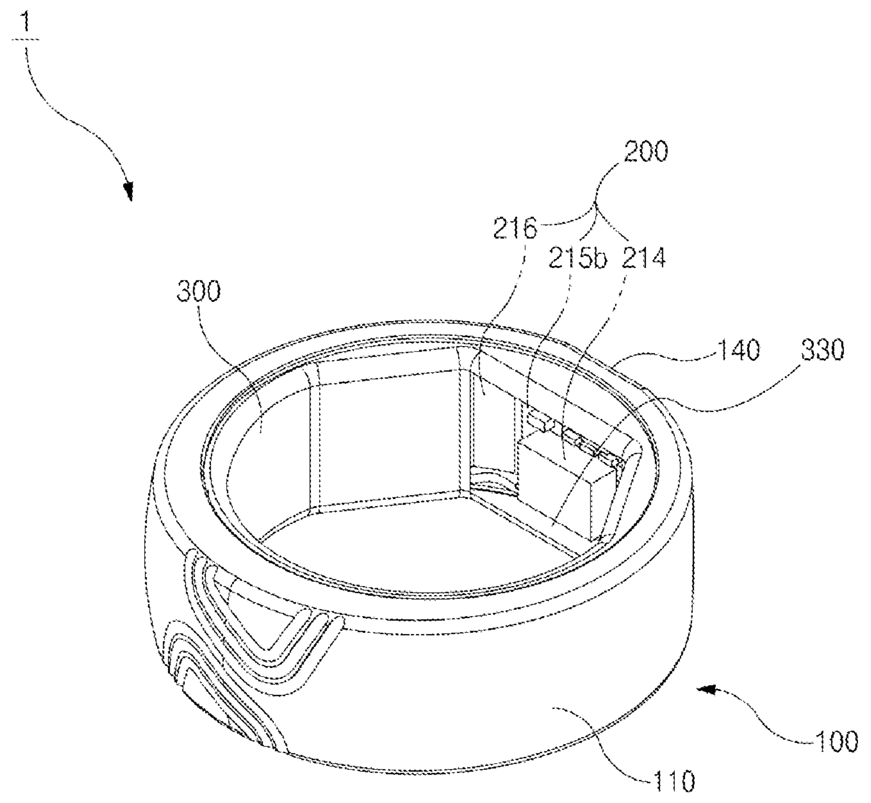
FIG. 3 is a perspective view showing a smart ring manufactured in the method of FIG. 1 according to another embodiment of the present invention.
Figure 4:
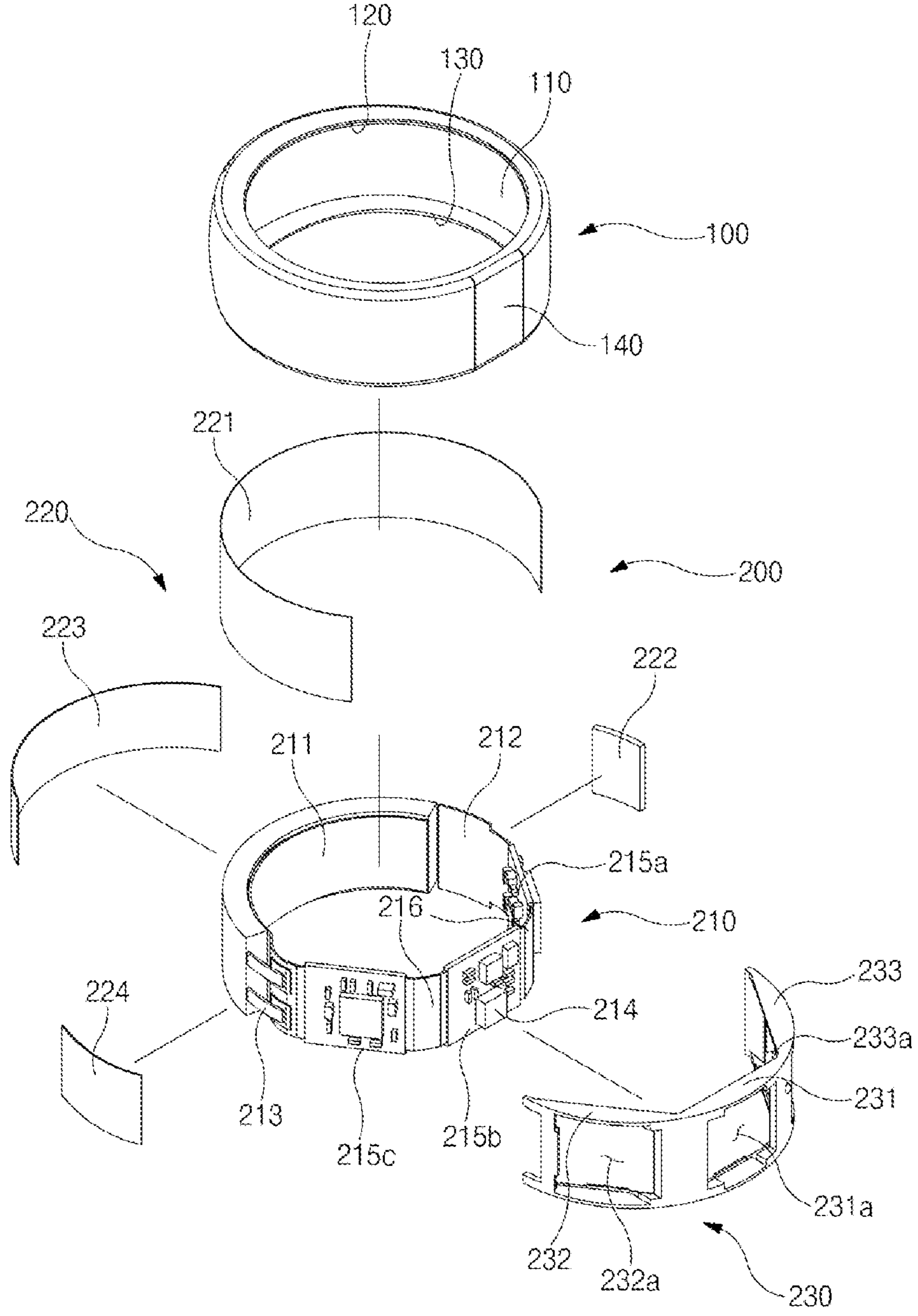
FIG. 4 is an exploded perspective view for explaining the configuration of a smart ring of the embodiments of the present invention and an embodiment of a part preparation process (S100) and a cover unit and sensor/communication module assembly manufacturing process (S200).

FIG. 1 is a flowchart illustrating a method of manufacturing a smart ring according to an embodiment of the present invention, FIG. 2 is a perspective view showing a smart ring manufactured in the method of FIG. 1 according to an embodiment of the present invention, and FIG. 3 is a perspective view showing a smart ring manufactured in the method of FIG. 1 according to another embodiment of the present invention. FIG. 4 is an exploded perspective view for explaining the configuration of a smart ring of the embodiments of the present invention and an embodiment of a part preparation process (S100) and a cover unit and sensor/communication module assembly manufacturing process (S200).

Referring to FIG. 1, the smart ring manufacturing method of the present invention includes: a part preparation process (S100) including an outer cover unit processing process (S110) and a sensor/communication module manufacturing process (S120); an outer cover unit and sensor/communication module assembly manufacturing process (S200); an inner molded unit processing process (S300); and a sensing window forming process (S400). When the sensing window forming process (S400) is completed, a conventional finishing process (S500) of impurity removing and polishing is performed to complete the method of manufacturing a smart ring 1 of the present invention.

As shown in FIGS. 2 and 3, it is a method of manufacturing a smart ring 1, in which the sensor/communication module 200 includes a sensor module 214, and a sensing window 330, which is an area that passes a signal or light needed for the sensor module to sense biological signals of a smart ring user, is formed on the inner surface of an inner molded unit 300 by processing an area on the inner surface of the inner molded unit 300, corresponding to the position where the sensor module 214 is installed, to be transparent.

Referring to FIGS. 2 and 3, the smart ring 1 manufactured by the method of manufacturing a smart ring 1 of the present invention has a basic configuration of an outer cover unit 100 having a ring shape of a smart ring and accommodating a sensor/communication module; a sensor/communication module 200 including a sensor module for sensing a biological signal of a smart ring wearer; and an inner molded unit 300 having a hole of a predetermined shape, into which a smart ring user's finger is inserted, inside the assembly of the ring-shaped outer cover unit 100 and the sensor/communication module 200.

A sensing window, which is an area that passes a signal or light needed for the sensor module 214 to sense biological signals of the smart ring user, is formed on the inner surface of the inner molded unit 300.

The embodiment of FIG. 2 is an embodiment in which the sensing window 330 is formed by processing the whole inner molded unit 300 to be transparent, and the embodiment of FIG. 3 is an embodiment in which the sensing window 330 is formed by processing only an area on the inner surface of the inner molded unit 300, corresponding to the position of the sensor module 214, to be transparent.

Referring to FIGS. 2 to 4, in the outer cover unit processing process (S110) of the part preparation process (S100), the outer cover unit 100 having a ring shape of a smart ring and accommodating the sensor/communication module is processed and manufactured. In this embodiment, the outer cover unit 100 may be manufactured using a metal material such as titanium or medical stainless steel.

However, according to embodiments, the outer cover unit 100 may be manufactured using various materials such as ceramics, plastic, wood, and the like without being limited to the metal material, and an appropriate known processing method may be selected and used according to the material.

Describing the detailed configuration of the outer cover unit 100 processed in this embodiment with reference to FIG. 4, the outer cover unit 100 of this embodiment is manufactured using a metal material such as titanium or medical stainless steel, and the outer cover unit 100 includes: an outer cover body 110 having a ring shape; an upper flange 120 provided on the top of the outer cover body 110; and a lower flange 130 provided on the bottom of the outer cover body 110. The outer cover unit 100 is processed to form a ring-shaped accommodation space surrounded by the inner surfaces of the outer cover body 110, the upper flange 120, and the lower flange 130, and the sensor/communication module 200 is accommodated and combined in the ring-shaped space.

In this embodiment, the outer cover unit 100 further includes a position guide 140 for guiding the outer cover body 110 to be disposed at a set position of a molding device 400 described below. The position guide 140 of the outer cover unit 100 guides the outer cover body 110 to be disposed at a set position of the molding device 400, and through this, accuracy and efficiency of the processes in the inner molded unit processing process can be improved, and product quality can be improved by reducing the defect rate.

As shown in FIG. 4, the position guide 140 may be formed as a flat area on the outer wall of the outer cover body 110, and according to embodiments, it may be formed in the shape of a groove or a protrusion, other than the flat area.

Referring to FIGS. 2 to 4, in the sensor/communication module manufacturing process (S120) of the part preparation process (S100), the sensor/communication module 200 including a sensor module for sensing biological signals of a smart ring user is manufactured, and in this embodiment, the sensor/communication module 200 is manufactured by connecting a plurality of PCB assemblies 215*a*, 215*b*, and 215*c*, in which electronic circuits such as the sensor module 214, a battery, other communication modules, and the like are installed, using bending members 216.

In this embodiment, the sensor module 214 includes an optical blood flow measurement sensor and may measure blood flow information of the wearer of the smart ring, and through the blood flow information, biological information such as heart rate, oxygen saturation, and the like may be measured.

Referring to FIG. 4, the detailed configuration of the sensor/communication module 200 manufactured in this embodiment may include a sensing/communication unit 210 and an attachment unit 220, and may further include a bracket unit 230.

As shown in FIG. 4, the sensor/communication module 200 may be manufactured in a ring shape corresponding to the ring-shaped accommodation space surrounded by the inner surfaces of the upper flange 120 and the lower flange 130 so as to be accommodated and combined at once in the ring-shaped space surrounded by the inner surfaces of the outer cover body 110, the upper flange 120, and the lower flange 130. In the sensor/communication module manufacturing process (S120) of the part preparation process (S100), the sensor/communication module 200 is manufactured in a ring shape that can be accommodated in correspondence to the ring-shaped accommodation space by combining the components described below.

To this end, the sensing/communication unit 210 includes: a base body 211 having a semicircular shape; a connection unit 212 having a semicircular shape and provided to be thinner than the base body 211, of which one side is coupled to the base body 211, and the other side is coupled to the plurality of PCB assemblies 215*a*, 215*b*, and 215*c*; the plurality of PCB assemblies 215*a*, 215*b*, and 215*c* of which one side is coupled to the connection unit 212; bending members 216 for connecting the PCB assemblies 215*a*, 215*b*, and 215*c*; and a connection member, of which one side is coupled to the base body 211, and the other side is coupled to the plurality of PCB assemblies 215*a*, 215*b*, and 215*c*, and a sensor module 214, a battery, a communication module, and other necessary electronic circuits are disposed in the plurality of PCB assemblies 215*a*, 215*b*, and 215*c*. In this embodiment, the sensor module 214 is installed in the central PCB assembly 215*b*, and includes an optical blood flow measurement sensor that measures, using light, heart rate or oxygen saturation at a body part, such as fingertip, through which an artery passes.

In this embodiment, a bracket unit 230 coupled to the connection unit 212 and the connection member 213 is further included, and the bracket unit 230 protects the plurality of PCB assemblies 215, and the sensor module 214, the battery, and the communication module installed therein, and allows the plurality of PCB assemblies 215*a*, 215*b*, and 215*c* to be installed at an accurate position.

As shown in FIG. 4, the attachment unit 220 of the sensor/communication module 200 includes: an inner attachment member 221 attached to the inner wall of the sensing/communication unit 210 to protect the sensor module 214, the battery, the communication module, and other necessary electronic circuits of the plurality of PCB assemblies 215; a first attachment member 222 coupled to the connection unit 212 to couple a third body 233 of the bracket unit 230 to the connection unit 212; a second attachment member 223 attached to the outer wall of the base body 211 to attach the base body 211 to the inner wall of the outer cover body 110; and a third attachment member 224 coupled to the area of the connection member 213 to attach the second body 232 of the bracket unit 230 to the area of the connection member 213.

The bracket unit 230 of the sensor/communication module 200 is attached to the sensing/communication unit 210 by the attachment unit 220 described above, and may protect the sensor module 214, the battery, the communication module, and other necessary electronic circuits of the plurality of PCB assemblies 215.

In this embodiment, as shown in FIG. 4, the bracket unit 230 includes: a first body 231 provided at a position corresponding to the plurality of PCB assemblies 215 and having a first hole 231*a* in which the central first PCB assembly 215*b* having the sensor module 214 installed therein is disposed; a second body 232 having a second hole 232*a* in which the right second PCB assembly 215*a* is disposed; and a third body 233 having a third hole 233*a* in which the left third PCB assembly 215*c* is disposed.

In this embodiment, the overall shape of the outer wall of the bracket unit 230 may be a semicircular shape as shown in FIG. 4.

In the outer cover unit and sensor/communication module assembly manufacturing process (S200), a ring-shaped assembly is formed by accommodating the sensor/communication module 200 in the ring-shaped inside of the processed outer cover unit 100, and in this embodiment, the accommodated sensor/communication module 200 is attached and fixed to the inner wall of the outer cover body 110 through the second attachment member 223 of the attachment unit 220 of the sensor/communication module 200.

In the inner molded unit processing process (S300), an inner molded unit 300 having a hole of a predetermined shape, into which a smart ring user's finger is inserted, is created inside the ring-shaped assembly.

In the present invention, the inner molded unit processing process (S300) is performed in a new method of creating the inner molded unit 300 by filling a molding member in the entire inner area of the ring-shaped assembly of the outer cover unit and the sensor/communication module, and cutting a hole of a predetermined shape at the center of the filled molding member.

The inner molded unit 300 is manufactured by molding a molding member of a transparent material, with which a coated transparent or translucent area may be generated by performing clear coating after molding and increasing transparency.

A transparent thermosetting plastic, such as transparent hard epoxy or the like, may be used as the molding member of a transparent material.

Figure 5:
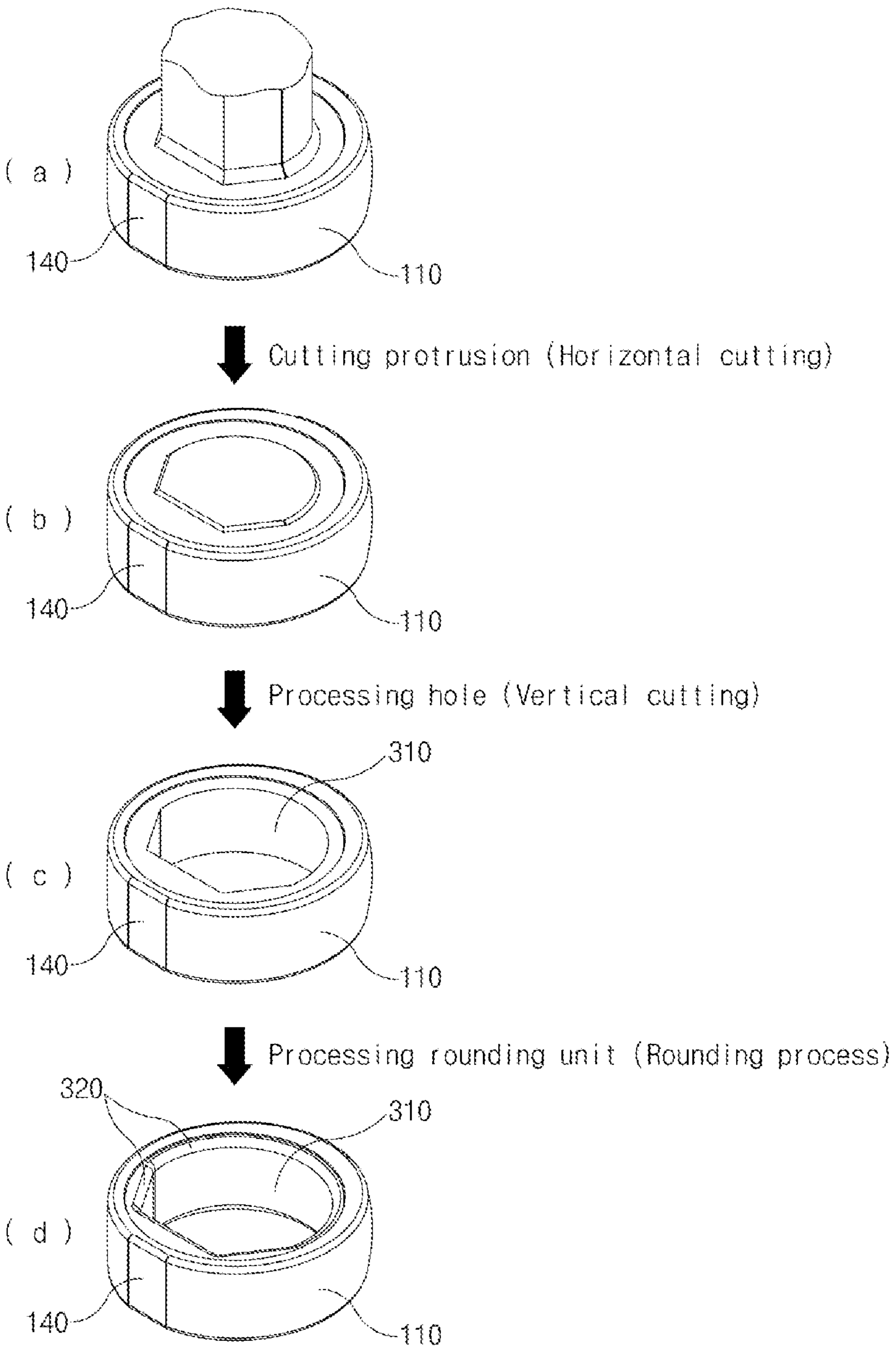
FIG. 5 is a view for explaining an embodiment of an inner molded unit processing process (S300) of the present invention.

FIG. 5 is a view for explaining an embodiment of an inner molded unit processing process (S300) of the present invention.

Figure 8:
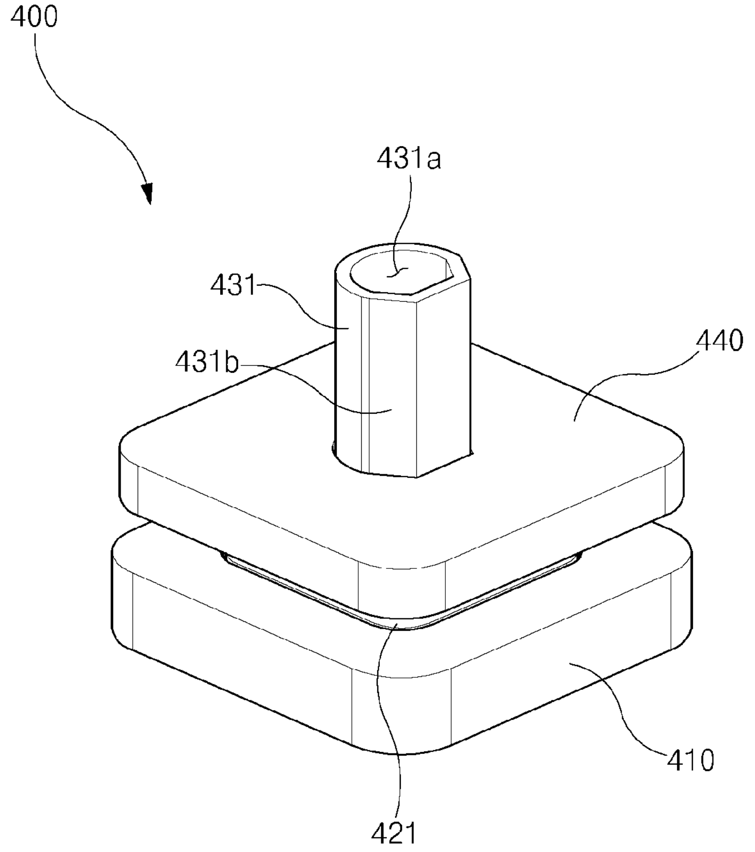
FIG. 8 is a perspective view schematically showing a molding device used for manufacturing a smart ring of embodiments of the present invention.
Figure 9:
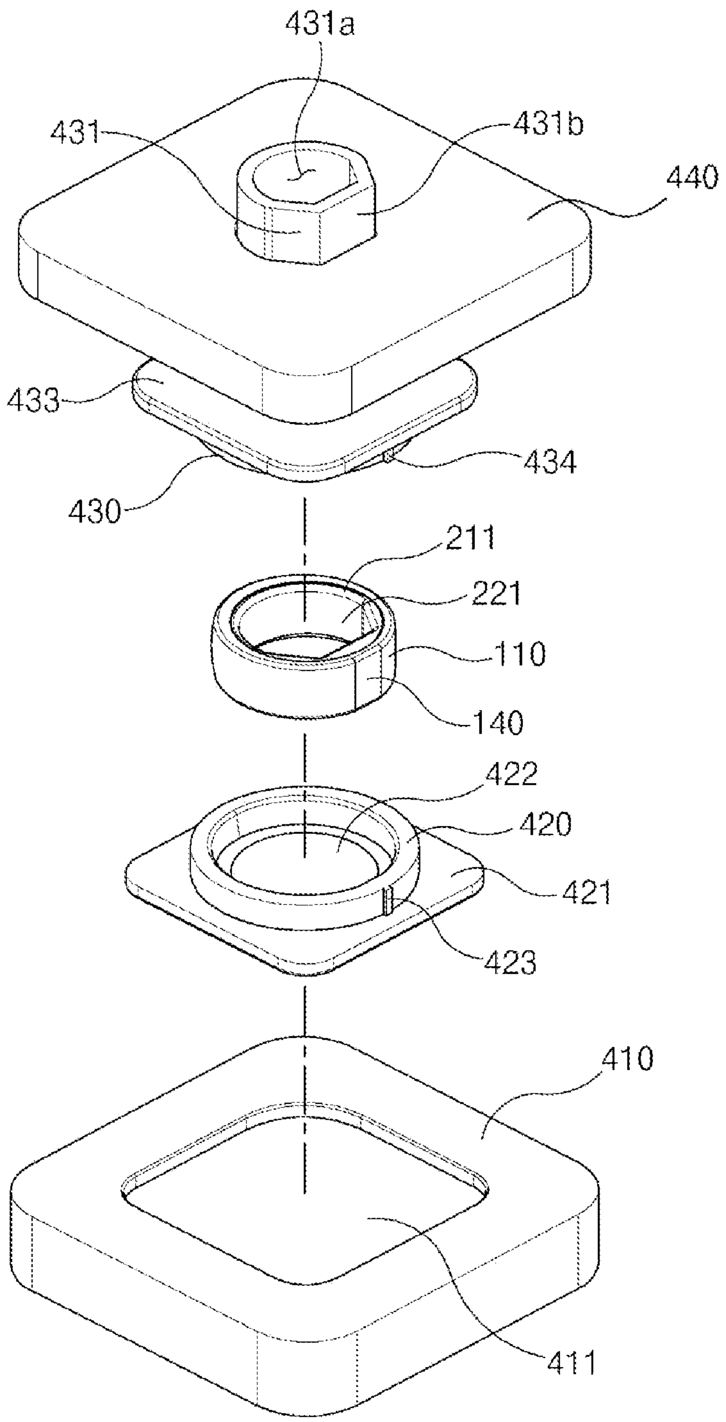
FIG. 9 is an exploded perspective view showing the molding device of FIG. 8.
Figure 10:
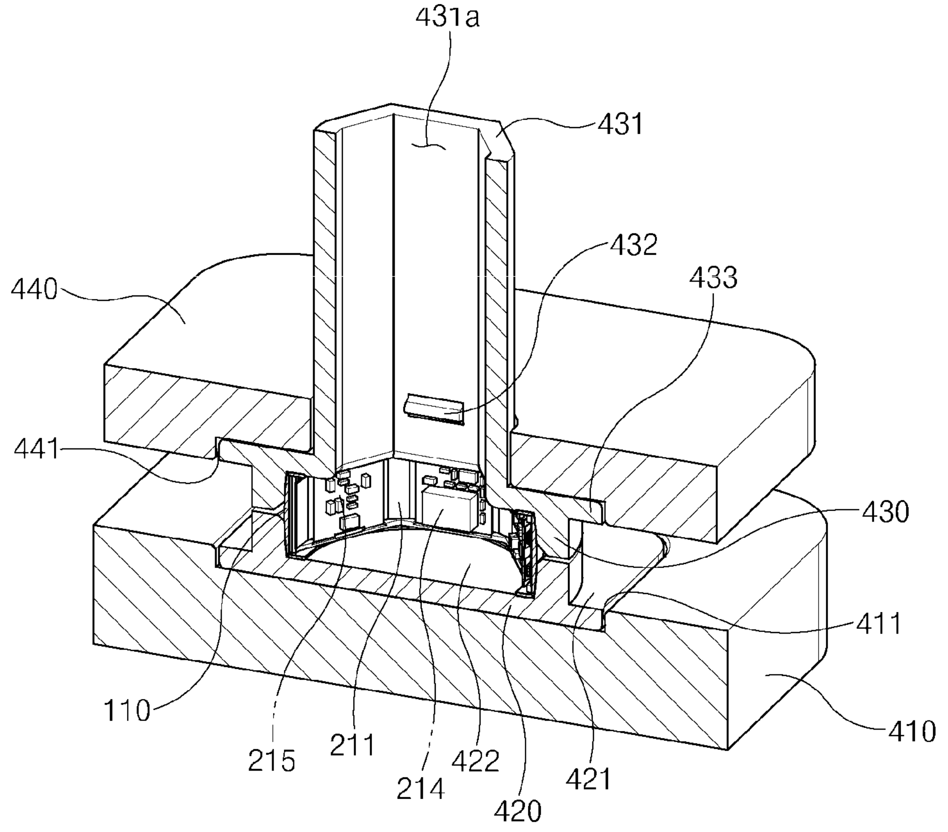
FIG. 10 is a cross-sectional view showing the molding device of FIG. 9.

Referring to FIG. 5, the inner molded unit processing process (S300) of this embodiment includes a molding member injection/curing process of injecting and curing a molding member in the entire inner area of the ring-shaped assembly of the outer cover unit and the sensor/communication module using the molding device of the embodiment of the present invention shown in FIGS. 8 to 10, and removing the molding device.

When the molding member injection/curing process is performed, a ring-shaped assembly of the sensor/communication module filled with the cured molding member in the entire inner area is obtained as shown in FIG. 5(*a*), and subsequently, a horizontal cutting process is performed to cut a molding member protrusion unit protruding from at least one among the top and bottom surfaces of the ring-shaped assembly of the sensor/communication module filled with the cured molding member.

As a result of performing the horizontal cutting process, a ring-shaped assembly of the sensor/communication module filled with the cured molding member in the entire inner area without having a protrusion is obtained as shown in FIG. 5(*b*).

Subsequently, a vertical cutting process is performed to process a hole of a predetermined shape at the center of the molding member filled in the ring-shaped assembly of the sensor/communication module filled with the molding member in the entire inner area without having a protrusion.

As a result of performing the vertical cutting process, an inner molded unit body 310 having an inner vertical surface is formed as shown in FIG. 5(*c*).

Subsequently, a rounding unit processing process is performed to form a rounding unit 320 by rounding at least one among the top and the bottom of the molded unit body 310.

As a result of performing the rounding unit processing process, the inner molded unit 300 configured of the molded unit body 310 and the rounding unit 320 is formed as shown in FIG. 5(*d*).

The horizontal cutting process, the vertical cutting process, and the rounding unit processing process may be performed through CNC machining.

The sensing window forming process (S400) is a process of forming a sensing window, which is an area that passes a signal or light needed for the sensor module to sense biological signals of a smart ring user, on the inner surface of the inner molded unit 300. It is a process of processing the inner surface of the inner molded unit 300, i.e., the entire or part of the wall surface of the hole created by the cutting process, to allow transmission of signals or light.

In this embodiment, as a clear coating layer is formed on the entire or part of the inner surface of the inner molded unit 300, which is a processed cut surface of the cured molding member of a transparent material, to improve transparency, signals or light transmitted and received by the sensor module may be transmitted, and an area optimized for transmission of the signals or light is formed.

In the present invention, as the position of the sensor module, i.e., when an optical blood flow measurement sensor is included, a position corresponding to the position of the light emitting unit and the light receiving unit of the optical blood flow measurement sensor, is clear-coated by performing transparency-adjusted clear coating on the entire or part of the inner surface of the inner molded unit 300, a transparent or translucent area with increased transparency is created as the sensing window 330.

In the present invention, as the area where the clear coating is applied can be adjusted by selectively performing a masking process on an area that will not be clear coated before the clear coating, the coated transparent or translucent area may create the sensing window 330 by easily performing clear coating at a desired position and range and increasing transparency.

In addition, since transparency of the clear-coated area may be adjusted by adjusting the type and mixing ratio of various known clear coating solutions, a transparent or translucent sensing window 330 having transparency optimized for the characteristics of the sensor module may be created.

The sensing window forming process (S400) may include: a masking process of attaching a masking member to an area of the smart ring to be processed, on which clear coating will not be performed; a primer coating process of forming a primer layer by applying a primer coating solution to the inner surface of the inner molded unit 300, on which clear coating will be performed; a process of forming a clear coating layer by applying a transparency-adjusted clear coating solution to a dried primer layer; and a drying and masking removal process of drying the clear coating layer and removing the masking member, and an area to be clear-coated may be adjusted in each embodiment by adjusting the range and shape of masking.

Figure 6:
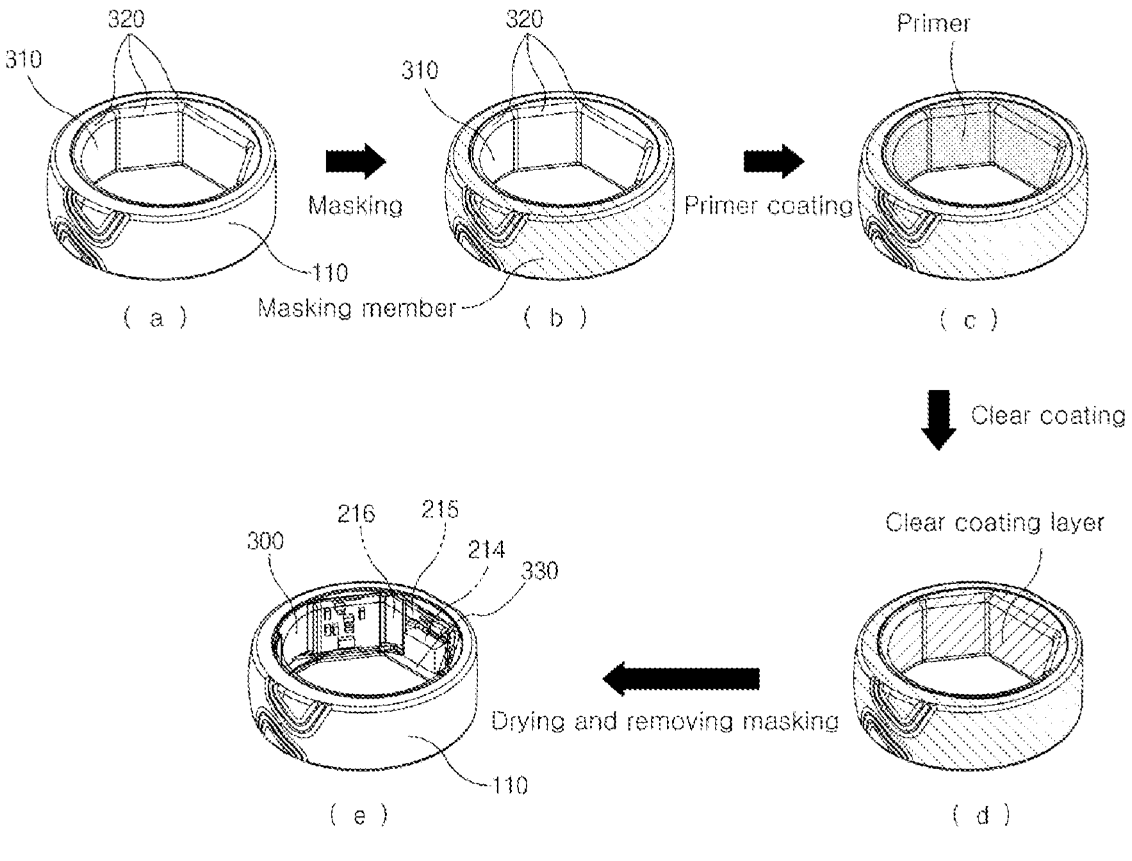
FIG. 6 is a view for explaining an embodiment of a sensing window forming process (S400) of the present invention.
Figure 7:
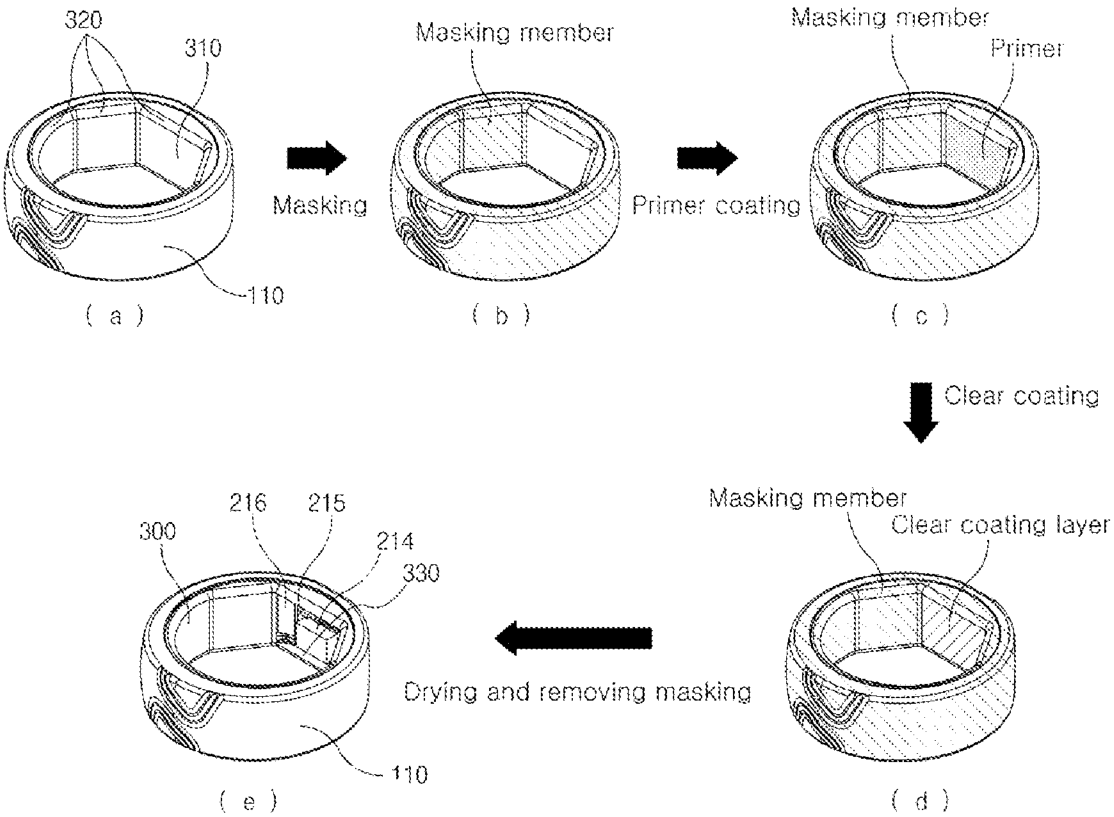
FIG. 7 is a view for explaining another embodiment of a sensing window forming process (S400) of the present invention.

FIG. 6 is a view for explaining an embodiment of a sensing window forming process (S400) of the present invention, and FIG. 7 is a view for explaining another embodiment of a sensing window forming process (S400) of the present invention.

In the sensing window forming process (S400) of the embodiment shown in FIG. 6, a sensing window 330, which is a transparent or translucent area that passes a signal or light needed for an area corresponding to the position of the sensor module to sense biological signals, is formed by performing transparency-adjusted clear coating on the entire inner surface of the inner molded unit 300. Through this embodiment, the sensing window 330 of the embodiment of FIG. 2 is formed.

Referring to FIG. 6, the sensing window forming process (S400) of this embodiment includes: a masking process of attaching a masking member to the outer cover unit, which an area of the smart ring of FIG. 6(*a*) to be processed, on which clear coating will not be performed; a primer coating process of forming a primer layer by applying a primer coating solution to the entire inner surface of the inner molded unit 300, on which clear coating will be performed, i.e., the surfaces of the molded unit body 310 and the rounding unit 320; a process of forming a clear coating layer by applying a transparency-adjusted clear coating solution to a dried primer layer; and a drying and masking removal process of drying the clear coating layer and removing the masking member.

Through this process, as shown in FIG. 6(*e*), an area corresponding to the position of the sensor module in the entire inner surface of the inner molded unit 300, which is processed to be transparent or translucent by clear coating, is formed as the sensing window 330.

In the sensing window forming process (S400) of the embodiment shown in FIG. 7, a sensing window 330, which is an area that passes a signal or light needed for an area corresponding to a clear-coated sensor module to sense biological signals, is formed by performing transparency-adjusted clear coating only in an area corresponding to the position of the sensor module of the inner molded unit 300. Through this embodiment, the sensing window 330 of the embodiment of FIG. 3 is formed.

Referring to FIG. 7, the sensing window forming process (S400) of this embodiment includes: a masking process of attaching a masking member to the area excluding the outer cover unit and the area corresponding to the position of the sensor module of the inner molded unit 300, which an area of the smart ring of FIG. 7(*a*) to be processed, on which clear coating will not be performed; a primer coating process of forming a primer layer by applying a primer coating solution to the surface of the inner molded unit 300, on which clear coating will be performed; a process of forming a clear coating layer by applying a transparency-adjusted clear coating solution to a dried primer layer; and a drying and masking removal process of drying the clear coating layer and removing the masking member.

Through this process, as shown in FIG. 7(*e*), an area corresponding to the position of the sensor module of the inner molded unit 300, which is processed to be transparent or translucent by clear coating, is formed as the sensing window 330.

In this embodiment, various paints may be used for the primer coating, and in this embodiment, a product named Eureka Primer #152 or UVILUX PRIMER #100-3 (NY) may be used.

For the clear coating, a desired level of transparency may be implemented by adjusting the ratio of mixing a glossy paint and a matte paint to adjust the transparency to be completely transparent by adjusting the mixing ratio of the glossy paint and the matte paint to 10:0 or to be translucent by adjusting the ratio of the glossy paint and the matte paint to 5:5.

In this embodiment, a product named HNP-UTT #3003 (P) CLEAR whose main component is Acryl polyol resin, a product named HNP-UVT #6011 CLEAR whose main component is Modified Acrylic Oligomers, or a product named UBchem CVM890SH top coat gloss (improved) whose main component is a reactive monomer may be selectively used as the glossy paint, and a product named HNP-UTT #3003 (P) MATT whose main component is Acryl polyol resin or a product named HNP-UTT #3003 (P) CLEAR whose main component is Acryl polyol resin may be selectively used as the matte paint.

Before the masking process, foreign matters such as dust or the like on the surface of the outer cover unit 100 may be removed in a way of neutralizing the static electricity charged in the outer cover unit 100 using ions, i.e., by performing an electricity elimination process in a method of consuming accumulated static electricity using ions.

Figure 11:
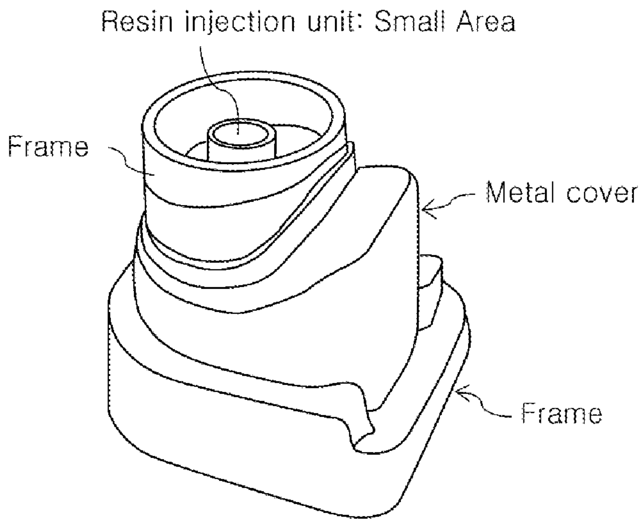
FIG. 11 is a view showing a molding device of the conventional technique.

In order to perform the molding member injection/curing process of the inner molded unit processing process (S300) of the new smart ring manufacturing method of the present invention described above, a molding device according to an embodiment of the present invention described below, which is different from the prior art molding device of FIG. 11, is developed and used.

FIG. 8 is a perspective view schematically showing a molding device used for manufacturing a smart ring of embodiments of the present invention, FIG. 9 is an exploded perspective view showing the molding device of FIG. 8, and FIG. 10 is a cross-sectional view showing the molding device of FIG. 8.

Referring to FIGS. 8 to 10, a molding device 400 used in the inner molded unit processing process (S300) of the smart ring manufacturing method of the present invention includes: an outer lower frame 410; an inner lower frame 420 coupled to the top of the outer lower frame 410, into which the lower portion of the assembly of the outer cover unit 100 and the sensor/communication module 200 described above is inserted and coupled; an inner upper frame 430 disposed on the top of the inner lower frame 420, into which the upper portion of the assembly of the outer cover unit 100 and the sensor/communication module 200 is inserted and coupled, and provided as an injection passage for the molding member; and an outer upper frame 440 disposed on the top of the inner upper frame 430 to fix the inner upper frame not to be spaced or separated.

As a first position guide protrusion 423 is provided on the outer wall of the inner lower frame 420 on the same vertical line as that of the position guide 140 and a second position guide protrusion 434, and the second position guide protrusion 434 is provided on the outer wall of the inner upper frame 430 on the same vertical line as that of the position guide 140 and the first position guide protrusion 423, coupling positions of the outer cover unit 100, the inner lower frame 420, and the inner upper frame 430 are guided in the molding member injection/curing process.

Referring to FIGS. 8 to 10, the outer lower frame 410 is provided with an outer lower groove 411 on the top surface as shown in FIG. 9, and an inner lower flange 421 of the inner lower frame 420 may be inserted and fit-coupled to the outer lower groove 411. As a result, the inner lower frame 420 may be fixed without being spaced or separated during a molding process.

In this embodiment, the outer lower frame 410 may be made of a material such as steel, stainless steel, or a plastic material, and this may also be applied to the inner lower frame 420.

The inner lower frame 420 may be inserted and fit-coupled to the outer lower groove 411 of the outer lower frame 410 to support the lower portion of the assembly of the outer cover unit 100 and the sensor/communication module 200.

In this embodiment, the inner lower flange 421 is provided on the bottom of the inner lower frame 420 as shown in FIGS. 9 and 10, and the inner lower flange 421 may be detachably inserted and fit-coupled to the outer lower groove 411.

In addition, in this embodiment, an inner groove 422 is provided on the top surface of the inner lower frame 420 as shown in FIGS. 9 and 10, and the lower portion of the assembly of the outer cover unit 100 and the sensor/communication module 200 may be inserted and fit-coupled to the inner groove 422.

Furthermore, in this embodiment, the first position guide protrusion 423 may be provided on the outer wall of the inner lower frame 420 as shown in FIG. 9. In this embodiment, the first position guide protrusion 423 is provided on the same vertical line as that of the position guide 140 of the outer cover unit 100 and the second position guide protrusion 434 of the inner upper frame 430 as shown in FIG. 9 to conveniently guide the coupling position of the outer cover unit 100 and the inner upper frame 430.

In addition, in this embodiment, the inner lower frame 420 may be made of a material containing silicon so as to be tightly attached to the surface of the outer lower frame 410 so that, when a molding member containing transparent hard epoxy is injected, the resin may not overflow and contaminate the outer lower frame 410, and to facilitate separation from the outer lower frame 410 after the molding member is cured. In this embodiment, silicon may have a hardness of 60 to 70 degrees.

The inner upper frame 430 may support the upper portion of the assembly of the outer cover unit 100 and the sensor/communication module 200, and the molding member may be injected into the outer cover unit 100.

In this embodiment, as shown in FIGS. 9 and 10, the inner upper frame 430 includes: an injection post 431 provided on the top as an injection passage of the molding member; an injection position protrusion 432 provided on the inner wall of the injection post 431 to guide an upper limit injection height of the molding member filled inside the injection post 431; an inner upper flange 433 provided on the bottom of the inner upper frame 430 to be inserted and fit-coupled to the outer upper groove 441 of the outer upper frame 440; and a second position guide protrusion 434 provided on the outer wall of the inner upper frame 430 on the same vertical line as that of the position guide 140 and the first position guide protrusion 423 to conveniently guide the coupling position of the inner upper frame 430.

In this embodiment, the injection post 431 is provided with an injection hole 431*a* as shown in FIGS. 9 and 10, and through the injection hole 431*a*, the molding member may be injected and cured in the outer cover unit 100 to which the sensor/communication module 200 is coupled. In addition, in this embodiment, a post guide 431*b* is provided on the outer wall of the injection post 431 as shown in FIG. 9, and the post guide 431*b* may be provided on the same vertical line as that of the second position guide protrusion 434, the position guide 140, and the first position guide protrusion 423.

As shown in FIG. 9, the outer upper frame 440 is detachably inserted and fit-coupled to the inner upper flange 433 through the outer upper groove 441 so that the inner upper frame 430 may not be spaced or separated during the molding process.

In comparison with the conventional molding device of FIG. 11, as the molding device 400 of this embodiment as described above may make the area of the molding member exposed to the outside wider as much as the wide area of the injection hole 431*a* in the inner frame structure progressed through overall molding, a large area is provided for air bubbles, generated by the use of the material of the molding member, to escape when the air bubbles are removed, and therefore, as the air bubbles may be easily discharged, the air bubbles can be removed quickly and more efficiently, compared to a molding device of the conventional technique having a small area exposed to the outside due to the small area of the injection hole. Accordingly, work efficiency and product quality related to transparency can be improved.

In the molding member injection/curing process of the inner molded unit processing process (S300), first, a molding member containing epoxy may be injected and cured in the assembly of the outer cover unit 100 and the sensor/communication module 200 using the molding device 400 of the above embodiment, and then an assembly of the outer cover unit 100 and the sensor/communication module 200 filled with the cured epoxy molding shown in FIG. 5(*a*) as a molding member can be obtained by removing each component of the molding device 400 when the epoxy is cured. Subsequently, the inner molded unit 300 is completed through the inner molded unit processing process (S300) described in relation to FIGS. 5 and 6.

Meanwhile, as shown in FIGS. 2 and 3, the smart ring 1 according to this embodiment manufactured in the method described above includes: an outer cover unit 100 having a ring shape of a smart ring and accommodating a sensor/communication module; the sensor/communication module 200 including a sensor module accommodated in the outer cover unit 100 to sense a biological signal of a smart ring user; and an inner molded unit 300 having a hole of a predetermined shape, into which a smart ring user's finger is inserted, and the outer cover unit 100 and the sensor/communication module 200 are combined to form a ring-shaped outer cover unit and sensor/communication module assembly, and the inner molded unit 300 is formed by filling a molding member in the entire inner area of the ring-shaped assembly and cutting a hole of a predetermined shape at the center of the filled molding member.

Referring to FIG. 4, the outer cover unit 100 includes: an outer cover body 110 having a ring shape; an upper flange 120 provided on the top of the outer cover body 110; and a lower flange 130 provided on the bottom of the outer cover body 110, and a ring-shaped accommodation space surrounded by the inner surfaces of the outer cover body 110, the upper flange 120, and the lower flange 130 is formed, and the sensor/communication module 200 may be accommodated and combined in the ring-shaped space.

Here, the sensor/communication module 200 is manufactured in a ring shape corresponding to the ring-shaped accommodation space surrounded by the inner surfaces of the upper flange 120 and the lower flange 130, and may be accommodated and combined in the ring-shaped space surrounded by the inner surfaces of the outer cover body 110, the upper flange 120, and the lower flange 130.

In this embodiment, the sensor/communication module 200 includes: a base body 211 having a semicircular shape; a connection unit 212 having a semicircular shape and provided to be thinner than the base body 211, of which one side is coupled to the base body 211, and the other side is coupled to the plurality of PCB assemblies 215*a*, 215*b*, and 215*c*; the plurality of PCB assemblies 215*a*, 215*b*, and 215*c* of which one side is coupled to the connection unit 212; bending members 216 for connecting the PCB assemblies 215*a*, 215*b*, and 215*c*; and a connection member, of which one side is coupled to the base body 211, and the other side is coupled to the plurality of PCB assemblies 215*a*, 215*b*, and 215*c*.

In addition, the outer cover unit 100 includes a position guide 140 for guiding the outer cover body 110 at a set position of the molding device 400.

Furthermore, the molding member that forms the inner molded unit 300 is a cured transparent thermosetting plastic.

Here, a sensing window 330, which is an area that passes a signal or light needed for the sensor module to sense biological signals of a smart ring user, may be formed in the entire or part of the wall surface of the hole created by cutting the inner surface of the inner molded unit 300.

Here, the sensing window 330 may be an area whose transparency is improved by a clear coating layer at a position corresponding to the sensor module on the inner surface of the inner molded unit 300, and the sensor module includes an optical blood flow measurement sensor, and the sensing window 330 is at a position corresponding to the sensor module, and may be a transparent or translucent area with improved transparency as a position corresponding to the position of the light emitting unit and the light receiving unit of the optical blood flow measurement sensor is clear-coated.

As described above, the present invention is not limited to the embodiments described above, and it is obvious to those skilled in the art that various modifications and variations can be made without departing from the spirit and scope of the present invention. Therefore, it should be said that such modifications or variations fall within the scope of the claims of the present invention.

DESCRIPTION OF SYMBOLS

1: Smart Ring
100: Outer cover unit 110: Outer cover body
120: Upper flange 130: Lower flange
140: Position guide 200: Sensor/communication module
210: Sensing/communication unit 211: Base body
212: Connection unit 213: Connection member
214: Sensor module 215: PCB assembly
216: Bending member 220: Attachment unit
221: Inner attachment member 222: First attachment member
223: Second attachment member 224: Third attachment member
230: Bracket unit 231: First body
231*a*: First hole 232: Second body
232*a*: Second hole 233: Third body
233*a*: Third hole 300: Inner molded unit
310: Molded unit body 320: Rounding unit
330: Sensing window
400: Molding device 410: Outer lower frame
411: Outer lower groove 420: Inner lower frame
421: Inner lower flange 422: Inner groove
423: First position guide protrusion 430: Inner upper frame
431: Injection post 431*a*: Injection hole
431*b*: Post guide 432: Injection position protrusion
433: Inner upper flange 434: Second position guide protrusion
440: Outer upper frame 441: Outer upper groove

The invention claimed is:

1. A smart ring manufacturing method comprising:
an outer cover unit processing process (S110) of processing and manufacturing an outer cover unit 100 having a ring shape of a smart ring and accommodating a sensor/communication module;
a sensor/communication module manufacturing process (S120) of manufacturing the sensor/communication module 200 including a sensor module for sensing a biological signal of a smart ring user;
an outer cover unit and sensor/communication module assembly manufacturing process (S200) of forming a ring-shaped outer cover unit and sensor/communication module assembly by accommodating the sensor/communication module 200 in a ring-shaped inside of the outer cover unit 100;
an inner molded unit processing process (S300) of creating an inner molded unit 300 having a hole of a predetermined shape, into which a smart ring user's finger is inserted, inside the ring-shaped outer cover unit and sensor/communication module assembly;
a sensing window forming process (S400) of forming a sensing window, which is an area that passes a signal or light needed for the sensor module to sense biological signals of the smart ring user, on an inner surface of the inner molded unit 300, wherein
in the inner molded unit processing process (S300), the inner molded unit 300 is created by filling a molding member in an entire inner area of the ring-shaped assembly, and cutting a hole of a predetermined shape at a center of the filled molding member.

2. The method according to claim 1, wherein the molding member of the inner molded unit 300 is a thermosetting plastic of a transparent material.

3. The method according to claim 1, wherein in the outer cover unit processing process (S110), the outer cover unit 100 is processed to include:
an outer cover body 110 having a ring shape;
an upper flange 120 provided on a top of the outer cover body 110; and
a lower flange 130 provided on a bottom of the outer cover body 110, and
a ring-shaped accommodation space surrounded by inner surfaces of the outer cover body 110, the upper flange 120, and the lower flange 130 is formed.

4. The method according to claim 3, wherein in the sensor/communication module manufacturing process (S120), the sensor/communication module 200 is manufactured in a ring shape that can be accommodated in correspondence to the ring-shaped accommodation space by combining components of the sensor/communication module 200.

5. The method according to claim 1, wherein the inner molded unit processing process (S300) includes:
a molding member injection/curing process of injecting and curing the molding member in the entire inner area of the ring-shaped assembly of the outer cover unit and the sensor/communication module and removing the molding device;
a horizontal cutting process of cutting a molding member protrusion unit protruding from at least one among top and bottom surfaces of the ring-shaped assembly of the sensor/communication module filled with the cured molding member in the entire inner area; and
a vertical cutting process of processing a hole of a predetermined shape at a center of the molding member filled in the ring-shaped assembly of the sensor/communication module filled with the molding member in the entire inner area without having a protrusion.

6. The method according to claim 5, further comprising a rounding unit processing process of forming a rounding unit 320 by rounding at least one among a top and a bottom of the molded unit body 310 of the inner molded unit 300.

7. The method according to claim 2, wherein in the sensing window forming process (S400), a sensing window 330, which is a transparent or translucent area that passes a signal or light needed for an area corresponding to a position of the sensor module to sense biological signals, is formed by performing transparency-adjusted clear coating on an entire inner surface of the inner molded unit 300.

8. The method according to claim 2, wherein in the sensing window forming process (S400), a sensing window 330, which is an area that passes a signal or light needed for an area corresponding to a clear-coated sensor module to sense biological signals, is formed by performing transparency-adjusted clear coating in an area corresponding to the position of the sensor module of the inner molded unit 300.

9. The method according to claim 8, wherein the sensing window forming process (S400) includes:
a masking process of attaching a masking member to an area of the smart ring to be processed, on which clear coating will not be performed;
a primer coating process of forming a primer layer by applying a primer coating solution to the inner surface of the inner molded unit 300, on which clear coating will be performed;
a process of forming a clear coating layer by applying a transparency-adjusted clear coating solution to a dried primer layer; and
a drying and masking removal process of drying the clear coating layer and removing the masking member.

10. The method according to claim 5, wherein the molding device includes:
an outer lower frame 410;

an inner lower frame 420 coupled to a top of the outer lower frame 410, into which a lower portion of the assembly of the outer cover unit 100 and the sensor/communication module 200 is inserted and coupled;

an inner upper frame 430 disposed on a top of the inner lower frame 420, into which an upper portion of the assembly of the outer cover unit 100 and the sensor/communication module 200 is inserted and coupled, and provided as an injection passage for the molding member; and an outer upper frame 440 disposed on a top of the inner upper frame 430 to fix the inner upper frame not to be spaced or separated, and the outer cover unit 100 includes a position guide 140 for guiding the outer cover body 110 at a set position of the molding device 400, wherein a first position guide protrusion 423 is provided on an outer wall of the inner lower frame 420 on the same vertical line as that of the position guide 140 and a second position guide protrusion 434, and the second position guide protrusion 434 is provided on an outer wall of the inner upper frame 430 on the same vertical line as that of the position guide 140 and the first position guide protrusion 423, in the molding member injection/curing process, coupling positions of the outer cover unit 100, the inner lower frame 420, and the inner upper frame 430 are guided using the position guide 140, the first position guide protrusion 423 and the second position guide protrusion 434.

11. The method according to claim 7, wherein the sensing window forming process (S400) includes:

a masking process of attaching a masking member to an area of the smart ring to be processed, on which clear coating will not be performed;

a primer coating process of forming a primer layer by applying a primer coating solution to the inner surface of the inner molded unit 300, on which clear coating will be performed;

a process of forming a clear coating layer by applying a transparency-adjusted clear coating solution to a dried primer layer; and a drying and masking removal process of drying the clear coating layer and removing the masking member.

* * * * *